US011590163B2

(12) United States Patent
Galaffu et al.

(10) Patent No.: US 11,590,163 B2
(45) Date of Patent: Feb. 28, 2023

(54) IRON-FORTIFIED FOOD COMPOSITION

(71) Applicant: SOCIETE DES PRODUITS NESTLE S.A., Vevey (CH)

(72) Inventors: Nicola Galaffu, Ornex (FR); Rachid Bel-Rhlid, Savigny (CH); Edwin Alberto Habeych Narvaez, Lausanne (CH); Sylvie Joelle Merinat, Moudon (CH); Brigitte Rey, Lussy (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 17/488,720

(22) Filed: Sep. 29, 2021

(65) Prior Publication Data

US 2022/0016161 A1    Jan. 20, 2022

Related U.S. Application Data

(62) Division of application No. 16/484,614, filed as application No. PCT/EP2018/053614 on Feb. 14, 2018, now Pat. No. 11,160,828.

(30) Foreign Application Priority Data

Feb. 14, 2017  (EP) .................................. 17156009

(51) Int. Cl.
*A61K 33/26* (2006.01)
*A23L 33/18* (2016.01)
(Continued)

(52) U.S. Cl.
CPC ................ *A61K 33/26* (2013.01); *A23L 2/66* (2013.01); *A23L 23/10* (2016.08); *A23L 33/165* (2016.08); *A23L 33/18* (2016.08); *A23L 33/185* (2016.08); *A61K 9/0056* (2013.01); *A61K 9/0095* (2013.01); *A61K 31/6615* (2013.01); *A61K 47/42* (2013.01); *A61P 7/06* (2018.01); *A23V 2002/00* (2013.01)

(58) Field of Classification Search
None
See application file for complete search history.

(56) References Cited

U.S. PATENT DOCUMENTS

| 4,216,144 | A | 8/1980 | Ashmead |
| 6,344,223 | B1 | 2/2002 | Rekhif et al. |
| 7,112,424 | B2 | 9/2006 | Rao et al. |

FOREIGN PATENT DOCUMENTS

| EP | 1743530 | 1/2007 |
| WO | 0051447 | 9/2000 |

(Continued)

OTHER PUBLICATIONS

Cai., "Common Feed Additives-Pollution-Free Use Technology", Jan. 31, 2003, p. 92.

(Continued)

*Primary Examiner* — Dominic Lazaro
(74) *Attorney, Agent, or Firm* — K&L Gates LLP

(57) ABSTRACT

The present invention relates to compositions for fortifying food and/or beverages with iron. More specifically, the present invention relates to compositions comprising Fe(III), phytic acid, a hydrolysed protein and an acidity regulator, which provide stable and soluble sources of iron for fortifying food and/or beverages.

19 Claims, 3 Drawing Sheets

(51) Int. Cl.

| | |
|---|---|
| *A23L 23/10* | (2016.01) |
| *A23L 33/165* | (2016.01) |
| *A23L 33/185* | (2016.01) |
| *A61P 7/06* | (2006.01) |
| *A23L 2/66* | (2006.01) |
| *A61K 9/00* | (2006.01) |
| *A61K 31/6615* | (2006.01) |
| *A61K 47/42* | (2017.01) |

(56) References Cited

FOREIGN PATENT DOCUMENTS

| WO | 0167897 | 9/2001 | | |
|---|---|---|---|---|
| WO | 2010086192 | 8/2010 | | |
| WO | WO-2010086192 A1 | * | 8/2010 | ............. A23L 23/00 |
| WO | 2013092336 | 6/2013 | | |
| WO | WO-2013092336 A1 | * | 6/2013 | ........... A23L 33/165 |
| WO | 2017037200 | 3/2017 | | |

OTHER PUBLICATIONS

Office Action Received for Application No. 201880010641.1, dated Feb. 8, 2022, 30 Pages(16 Pages of English Translation and 14 Pages of Official Copy).

Rao et al. "Studies on Iron Chelation by Phytate and the Influence of Other Mineral Ions on it" Nutrition Reports International, Oct. 1983, vol. 28, No. 4, pp. 771-782.

Graf et al. "Effects of Phytate on Mineral Bioavailability in Mice" The Journal of Nutrition, 1984, vol. 114, pp. 1192-1198.

Mintel "Breakfast Milk Powder with Iron, Zinc and Calcium" Sep. 2014, 3 pages, XP002769252.

* cited by examiner

IRON-FORTIFIED FOOD COMPOSITION

CROSS REFERENCE TO RELATED APPLICATIONS

The present application is a divisional of U.S. patent application Ser. No. 16/484,614 filed Aug. 8, 2019, which is a National Stage of International Application No. PCT/EP2018/053614 filed Feb. 14, 2018, which claims priority to European Patent Application No. 17156009.7 filed Feb. 14, 2017, the entire contents of which are incorporated herein by reference.

FIELD OF THE INVENTION

The present invention relates to compositions for fortifying food and/or beverages with iron. More specifically, the present invention relates to compositions comprising Fe(III), phytic acid, a hydrolysed protein and an acidity regulator, which provide stable and soluble sources of iron for fortifying food and/or beverages.

BACKGROUND TO THE INVENTION

Nutritional mineral deficiencies (also referred to as micronutrient malnutrition) affect a large proportion of the human population and are particularly widespread in developing countries. Deficiency in iron is especially common, affecting more than two billion people world-wide, and is the only nutrient deficiency that is significantly prevalent in industrialised countries. Iron deficiency is associated with a range of health problems, including impairment of work performance, increased maternal and child mortality, and poor cognitive development in children.

Iron deficiencies originate when physiological requirements are not met by mineral absorption from the diet, for example due to low iron bioavailability. Dietary iron bioavailability may be low, for example, in populations having monotonous plant-based diets with little meat. Indeed, a major cause of low iron bioavailability is related to the presence of anti-nutritional factors that are naturally present in cereals and legumes. These factors form insoluble complexes with iron and interfere with its absorption.

Fortifying food with iron is a well-known approach to increase dietary iron intake, but can pose a number of difficulties. A significant problem is caused by the general incompatibility between bioavailability and stability of iron compounds. Typically, the most bioavailable iron compounds (e.g., ferrous sulphate) are the most reactive within the food matrix. As such, fortifying foods with iron can lead to a number of undesirable changes in properties of the food, in particular organoleptic properties of the food. For example, iron can accelerate oxidation reactions, adversely altering a food's flavour, and iron can also form complexes with phenolic chromophore compounds, leading to unwanted colour changes in the food.

For example, ferrous (i.e. Fe(II)) sulphate, which is a reference iron compound for food fortification in humans in terms of high absorption, causes sensory changes in the food vehicle in the presence of polyphenols or high amounts of unsaturated lipids. In contrast, more stable iron sources, which are typically water-insoluble (e.g. ferric (i.e. Fe(III)) pyrophosphate), have relatively low bioavailability compared to water-soluble compounds.

A number of approaches have been taken during attempts to improve iron fortification of foods. Encapsulated ferrous sulphate has been considered, because it could provide a bioavailable iron source while maintaining stability through encapsulation of the formulation. However, bioavailability is highly dependent on the coating used and in many cases bioavailability of the coated iron source is reduced. Encapsulation also increases production costs. Moreover, most coatings used for encapsulation, which are often lipid based, give rise to problems associated with melting during the different heat treatment stages of the manufacture of many food products.

Alternative approaches have used iron-containing nanoparticles that have been stabilised with biopolymers (EP 1743530), or ferric sodium EDTA (ethylenediaminetetraacetic acid), which has good bioavailability and stability (US 2005/0053696), for iron fortification. However, the use of nanoparticles and EDTA in food products is meeting with increased consumer resistance. Furthermore, sodium iron EDTA is expensive and not stable in all food matrices (e.g. chicken bouillon).

Accordingly, there remains a significant need for compositions and methods that enable fortification of foods and beverages with iron. In particular, there remains a need for compositions and methods that provide a soluble, preferably bioavailable source of iron that has minimal effect on the organoleptic properties of foods.

Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

An object of the present invention is to improve the state of the art and to provide an improved solution for the iron fortification of food and beverages, or at least to provide a useful alternative. The object of the present invention is achieved by the subject matter of the independent claims. The dependent claims further develop the idea of the present invention.

The present inventors have surprisingly found that water-soluble complexes of Fe(III) can be prepared using phytic acid in the presence of hydrolysed protein. Although water-soluble Fe(II):phytic acid complexes are known, complexes of Fe(III) with phytic acid were previously regarded as highly insoluble. Indeed, the use of phytic acid in food products has previously been avoided due to its potential for binding multivalent cations. The resulting complexes are usually insoluble under physiological conditions, with the result that digestion by humans is difficult. Consequently, phytic acid has traditionally been considered as an antinutrient.

Moreover, the present inventors have found that the compositions of the present invention can be used to fortify food and beverages with little effect on their organoleptic properties. In particular, the present inventors have found that fruit or vegetable-containing foods and bouillon, which were previously regarded as difficult to fortify with iron, may be fortified with the compositions of the present invention with minimal effect on their colour. While not wishing to be bound by theory, this may be due to Fe(III) exhibiting greater stability than the soluble Fe(II) compositions that are commonly used (e.g. ferrous sulphate).

Accordingly, in one aspect the present invention provides a composition for fortifying food and/or beverages comprising a complex of Fe(III), phytic acid, hydrolysed protein and an acidity regulator. In a second aspect the invention provides a composition for fortifying food and/or beverages wherein the composition is obtainable by (for example obtained by) mixing an Fe(III) compound, phytic acid, hydrolysed protein and an acidity regulator. In a third aspect the invention provides the use of a composition comprising a complex of Fe(III), phytic acid, hydrolysed protein and an acidity regulator for fortifying a food or beverage product with iron. In a further aspect the invention provides a food or beverage product comprising a composition comprising a complex of Fe(III), phytic acid, hydrolysed protein and an acidity regulator. In a further aspect the invention provides a method of preparing a water-soluble composition, wherein the method comprises the steps:

(a) mixing in an aqueous solution a source of Fe(III), phytic acid, hydrolysed protein and an acidity regulator; and (b) optionally heating the mixture.

DETAILED DESCRIPTION OF THE INVENTION

Figure 1:
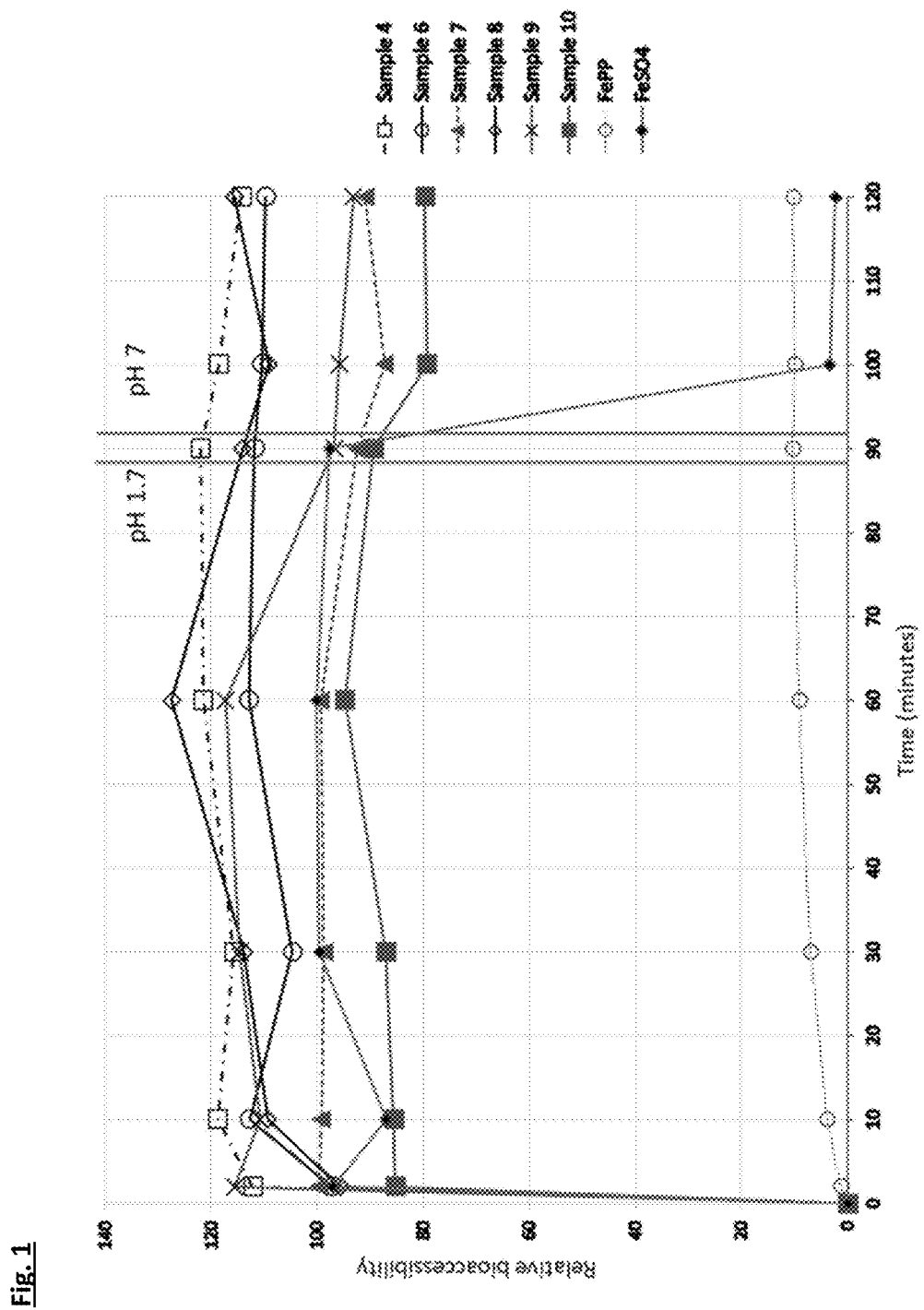
FIG. 1 is a plot of percentage relative bioaccessibility against time in minutes, as described in Example 3; Sample 4 (□), Sample 6 (○), Sample 7 (▲), Sample 8 (◇), Sample 9 (X), Sample 10 (■), FeSO$_4$ (○) and Fe pyrophosphate (◆).

Consequently the present invention relates in part to a composition for fortifying food and/or beverages comprising a complex of Fe(III), phytic acid, hydrolysed protein and an acidity regulator. The composition of the invention may comprise Fe(III) ions of which some or all are in the form of a complex with some or all of the phytic acid. The composition of the invention may comprise Fe(III) ions of which some or all are in the form of a complex with some or all of the phytic acid and with some or all of the hydrolysed protein. The composition of the invention may comprise Fe(III) ions of which some or all are in the form of a complex with some or all of the phytic acid, with some or all of the hydrolysed protein, and with some or all of the acidity regulator. The composition of the invention may comprise Fe(III) ions of which some or all are in the form of a water-soluble complex with some or all of the phytic acid. The composition of the invention may comprise Fe(III) ions of which some or all are in the form of a water-soluble complex with some or all of the phytic acid and with some or all of the hydrolysed protein. The composition of the invention may comprise Fe(III) ions of which some or all are in the form of a water-soluble complex with some or all of the phytic acid, with some or all of the hydrolysed protein, and with some or all of the acidity regulator.

The compositions of the invention may be any compositions that are suitable for ingestion by animals, preferably humans. The compositions may be ingested directly, however preferably the compositions of the invention are for use in fortifying foods and/or beverages with iron, i.e. increasing the amount of bioavailable iron in the food or beverage.

Fe(III) ions are iron ions of the +3 oxidation state. They may also be referred to as $Fe^{3+}$ ions or ferric ions. Fe(II) ions are iron ions of the +2 oxidation state. They may also be referred to as $Fe^{2+}$ ions or ferrous ions.

Sources of Fe(III) that may be used to produce the complexes or compositions of the present invention are not particularly limited, provided that they are suitable for ingestion by animals, preferably humans (e.g. are non-toxic). Example sources of Fe(III) include Fe(III) sulphate, Fe(III) citrate, Fe(III) diphosphate, Fe(III) saccharate, Fe(III) sodium diphosphate, Fe(III) choline citrate, Fe(III) ammonium citrate and Fe(III) chloride. Preferably, the source of Fe(III) is Fe(III) sulphate.

Phytic acid is a naturally-occurring compound found, for example, in grains, legumes, seeds and nuts in the form of phytates or phytic acid itself. Phytic acid compounds provide the principal plant storage form of phosphorus.

As used herein, "phytic acid" refers to a myo-inositol phosphate, i.e. myo-inositol monophosphate (InsP), myo-inositol bisphosphate (InsP$_2$), myo-inositol triphosphate (InsP$_3$), myo-inositol tetrakisphosphate (InsP$_4$), myo-inositol pentakisphosphate (InsP$_5$) or myo-inositol hexakisphosphate (InsP$_6$). Preferably, the phytic acid is myo-inositol hexakisphosphate.

myo-Inositol hexakisphosphate has the structure:

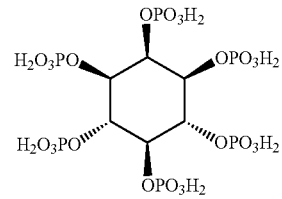

Advantageously, phytic acid may be regarded as a natural ingredient for delivering highly bioavailable iron, because it can be readily obtained from natural sources. For example, sources of phytic acid include cereals (e.g. wheat, corn, oat, barley, sorghum, millets, rice and bran), beans (e.g. peas, lentils, white beans and soybeans), tubers (e.g. potato, yam, sweet potato and sugar beet), fruit (e.g. plantain, dates, strawberry and avocado), leafy vegetables (e.g. spinach, red cabbage, okra, cauliflower, carrots and tomato), nuts (e.g. hazelnut, walnut, almond and cashew), and other foods such as coconut, sesame seeds and coriander. Contrary to the other crops, in corn, phytic acid is mostly in the germ.

In an embodiment, the invention provides a composition for fortifying food and/or beverages wherein the composition is obtainable (for example obtained) by mixing an Fe(III) compound, phytic acid, hydrolysed protein and an acidity regulator. The features of the composition may be as described herein for the compositions and methods of the invention.

The hydrolysed protein according to the composition or method of the present invention may be hydrolysed plant or animal protein. The hydrolysed animal protein according to the composition or method of the invention may be hydrolysed meat protein or hydrolysed milk protein. The hydrolysed protein according to the composition or method of the invention may be selected from the group consisting of hydrolysed corn protein, hydrolysed wheat protein, hydrolysed soy protein, hydrolysed pea protein and combinations of these. The protein may be hydrolysed enzymatically or chemically. The hydrolysed protein according to the composition or method of the invention may be acid-hydrolysed plant protein or enzymatically hydrolysed plant protein. An example of acid-hydrolysis would be the application of 6 M HCl at 120° C. for 24 hours. Enzymatic hydrolysis may for example be performed using endopeptidases (e.g. Alcalase®), exopeptidases (e.g. Flavourzyme®), or a mixture of endo and exopeptidases.

Hydrolysed plant protein products have a good acceptance in food products, they may be used to round off the taste of soups, sauces, meat products, snacks, and other dishes, as well as for the production of ready-to-cook soups and bouillons. It is therefore advantageous that such a well-accepted ingredient may be used to form a stable complex with which to fortify food and beverage products.

The hydrolysed protein according to the composition or method of the present invention may be protein hydrolysed to at least 10 w/w %, for example at least 20 w/w %. The hydrolysed protein according to the composition or method of the present invention may be protein hydrolysed to between 10 and 100 w/w %, for example between 10 and 90 w/w %, for example between 20 and 80 w/w %. The hydrolysed protein according to the composition or method of the present invention may be protein hydrolysed to between 70 and 100 w/w %, for example an acid hydrolysed protein hydrolysed to between 70 and 100 w/w %. The hydrolysed protein according to the composition or method of the present invention may be protein hydrolysed to between 20 and 30 w/w %, for example an enymatically hydrolysed protein hydrolysed to between 20 and 30 w/w %. The term "hydrolysed to 10 w/w %" in the context of the present invention means that 10 w/w % of the original quantity of protein has been hydrolysed, for example hydrolysed to a mixture comprising free peptides and free amino acids. The term "hydrolysed to 10 w/w %" is equivalent to "hydrolysed to an extent of 10 w/w %". Terms with other numerical values for the w/w % of hydrolysis are to be interpreted in the same manner. The hydrolysed protein according to the composition or method of the present invention may be protein hydrolysed to 100 w/w %, for example it may comprise free peptides and free amino acids but essentially no non-hydrolysed proteins. Different hydrolysis conditions will produce different mixtures of free peptides, free amino acids and non-hydrolysed proteins. The hydrolysed protein according to the composition or method of the present invention may comprise a mixture of free amino acids, free peptides and non-hydrolysed proteins. The hydrolysed protein according to the composition or method of the present invention may comprise between 15 and 45 wt. % free amino acids, for example it may be an enzymatically hydrolysed protein comprising between 15 and 45 wt. % free amino acids. The hydrolysed protein according to the composition or method of the present invention may comprise between 65 and 85 wt. % free amino acids, for example it may be an acid hydrolysed protein comprising between 65 and 85 wt. % free amino acids.

The hydrolysed protein according to the composition or method of the present invention may comprise amino acids selected from the group consisting of histidine, arginine, lysine, glycine, aspartic acid, glutamic acid, glutamine, proline and combinations thereof. The hydrolysed protein according to the composition or method of the present invention may be a hydrolysed plant protein (for example an enzymatically hydrolysed plant protein) and comprise at least 1 mg/g of histidine, at least 10 mg/g arginine, at least 10 mg/g lysine, at least 10 mg/g glycine, at least 30 mg/g aspartic acid, at least 30 mg/g glutamine, and at least 10 mg/g proline. The hydrolysed protein according to the composition or method of the present invention may be a hydrolysed plant protein (for example an enzymatically hydrolysed plant protein) and comprise at least 1 mg/g (for example at least 2 mg/g) of histidine and at least 10 mg/g (for example at least 20 mg/g) of glycine. The hydrolysed protein according to the composition or method of the present invention may be a hydrolysed plant protein (for example an enzymatically hydrolysed plant protein) and comprise at least 1 mg/g (for example at least 2 mg/g) of histidine. The hydrolysed protein according to the composition or method of the present invention may be a hydrolysed plant protein (for example an acid hydrolysed plant protein) and comprise at least 10 mg/g of histidine, at least 50 mg/g arginine, at least 50 mg/g lysine, at least 30 mg/g glycine, at least 90 mg/g aspartic acid, at least 100 mg/g glutamine, and at least 30 mg/g proline. The hydrolysed protein according to the composition or method of the present invention may be a hydrolysed plant protein (for example an acid hydrolysed plant protein) and comprise at least 10 mg/g (for example at least 15 mg/g) of histidine and at least 30 mg/g (for example at least 35 mg/g) glycine. The hydrolysed protein according to the composition or method of the present invention may be a hydrolysed plant protein (for example an acid hydrolysed plant protein) and comprise at least 10 mg/g (for example at least 15 mg/g) of histidine.

The acidity regulator according to the composition or method of the present invention may be any acidity regulator commonly used in food. The acidity regulator may for example be a sodium salt of sorbic acid, acetic acid, benzoic acid, propionic acid or formic acid. The acidity regulator may for example be selected from the group consisting of tri sodium phosphate, tri potassium phosphate, sodium hydrogen phosphate, potassium hydrogen phosphate, sodium dihydrogen phosphate, potassium dihydrogen phosphate, sodium carbonate, potassium carbonate, calcium carbonate, sodium bicarbonate, potassium bicarbonate, sodium lactate, potassium lactate, sodium citrate (mono, bis and tris), potassium citrate (mono, bis and tris), sodium malonate and potassium malonate. The acidity regulator may be an ammonium salt, for example the acidity regulator may be selected from the group consisting of ammonium hydroxide; ammonium carbonate; ammonium phosphate dibasic; ammonium sodium phosphate dibasic and triammonium phosphate. The acidity regulator may be ammonium hydroxide. The composition may be free from compounds comprising a carboxylic acid moiety other than those compounds comprised within the hydrolysed protein.

The composition according to the invention may be in the form of an aqueous solution or a water-soluble solid. The complex comprised within the composition of the invention may be in the form of an aqueous solution or a water-soluble solid. There are many advantages of providing an iron fortificants in a soluble complex. Digestion of complexes that are insoluble under physiological conditions is difficult, with the result that the iron is not taken up by the body. Soluble complexes are also easier to disperse in food and beverage products, avoiding problems of sedimentation and gritty mouthfeel. The water-soluble compositions of the invention include compositions that are almost entirely soluble in aqueous solution, i.e. dissolve to an extent that a solution retaining a haze is produced. In one embodiment, at least 70%, 75%, 80%, 85%, 90%, 91%, 92%, 93%, 94%, 95%, 96%, 97%, 98% or 99% by weight of the composition dissolves in aqueous solution. Preferably, the composition dissolves completely in aqueous solution.

The mass ratios of the components of the composition may be any ratios that provide a water-soluble composition.

In one embodiment, the mass ratio of phytic acid to Fe(III) is about 0.5:1 to about 125:1; the mass ratio of phytic acid to acidity regulator is about 0.1:1 to about 40:1; and/or the mass ratio of phytic acid to hydrolysed protein is about 0.5:1 to about 10:1.

In one embodiment, the mass ratio of phytic acid to Fe(III) is about 0.5:1 to about 125:1. In another embodiment, the mass ratio of phytic acid to Fe(III) is about 0.5:1 to about 50:1. In another embodiment, the mass ratio of phytic acid to Fe(III) is about 1:1 to about 20:1. In another embodiment, the mass ratio of phytic acid to Fe(III) is about 2:1 to about 15:1. In another embodiment, the mass ratio of phytic acid to Fe(III) is about 3:1 to about 10:1. The mass ratio of phytic acid to Fe(III) may be about 7:1. For calculating the mass ratio of phytic acid to Fe(III) the mass of the Fe(III) itself is taken, rather than the mass of any compound comprising it.

In one embodiment the molar ratio of phytic acid to Fe(III) is about 0.25:1 to about 10:1. In another embodiment the molar ratio of phytic acid to Fe(III) is about 0.3:1 to 1:1. In another embodiment the molar ratio of phytic acid to Fe(III) is about 0.6:1.

In one embodiment, the mass ratio of phytic acid to the acidity regulator is about 0.1:1 to about 40:1. In another embodiment, the mass ratio of phytic acid to the acidity regulator is about 0.1:1 to about 3:1. In another embodiment, the mass ratio of phytic acid to the acidity regulator is about 0.5:1 to about 2.5:1. In another embodiment, the mass ratio of phytic acid to the acidity regulator is about 0.8:1 to about 2:1. In another embodiment, the mass ratio of phytic acid to the acidity regulator is about 1:1 to about 1.5:1. In another embodiment, the mass ratio of phytic acid to the acidity regulator is about 1.3:1.

In one embodiment, the molar ratio of phytic acid to the acidity regulator is about 0.005:1 to about 2:1. In another embodiment, the molar ratio of the phytic acid to the acidity regulator is about 0.01:1 to about 1:1. In another embodiment, the molar ratio of the phytic acid to the acidity regulator is about 0.07:1.

In one embodiment, the molar ratio of the acidity regulator to Fe(III) is about 4:1 to about 30:1.

In another embodiment, the molar ratio of the acidity regulator to Fe(III) is about 4.4:1 to about 15:1. In another embodiment, the molar ratio of the acidity regulator to Fe(III) is about 4.4:1 to about 10:1. In another embodiment, the molar ratio of the acidity regulator to Fe(III) is about 4.4:1 to about 7.5:1.

In one embodiment, the mass ratio of the phytic acid to hydrolysed protein is about 10:1 to about 0.1:1. In another embodiment, the mass ratio of the phytic acid to hydrolysed protein is about 8:1 to about 0.5:1. In another embodiment, the mass ratio of the phytic acid to hydrolysed protein is about 5:1 to about 0.8:1. In another embodiment, the mass ratio of the phytic acid to hydrolysed protein is about 4:1 to about 1:1. In another embodiment, the mass ratio of the phytic acid to hydrolysed protein is about 2.5:1. The hydrolysed protein may have a degree of hydrolysis of at least 10 w/w % (for example at least 20 w/w %).

In one embodiment the mass ratio of phytic acid to Fe(III) may be between 5 and 10 to 1, the mass ratio of phytic acid to hydrolysed protein may be between 1 and 3.5 to 1, and the acidity regulator being ammonium hydroxide may be added in an amount to adjust the pH to between 6.5 and 7.5 wherein the hydrolysed protein is hydrolysed to an extent of greater than 20 w/w %. Such compositions are effective at fortifying food and/or beverages without excessive ingredient cost.

In one embodiment, the composition is in the form of an aqueous solution or a water-soluble solid. The composition in the form of an aqueous solution may comprise high concentrations of the complex and remain stable. For example the composition in the form of an aqueous solution may comprise at least 10 wt. % complex in solution, for example at least 20 wt. % complex in solution, for example at least 30 wt. % complex in solution.

The aqueous solution composition may be in the form of a concentrated stock solution for addition to food and/or beverage products, such as water (e.g. bottled water).

The solid composition may be in the form of a powder or granules. A powder composition may be contained in a sachet. A powder composition according to the present invention may be used to sprinkle onto a food or beverage. In one embodiment, the composition is in the form of a sachet containing a powder, wherein the powder can be dispersed into a beverage (e.g. water, fruit juice or milk) to provide a palatable nutrient liquid for oral administration.

In another aspect, the present invention provides the use of the composition of the invention for fortifying a food or beverage product with iron. The present invention may provide the use of the composition of the invention for fortifying a food or beverage product with iron when the food or beverage is to be co-ingested with an inhibitory meal.

In one embodiment, the use of the compositions of the invention reduces the effect of iron fortification on the organoleptic properties of the food or beverage (e.g. in comparison to other iron compositions, such as ferrous sulphate or ferric pyrophosphate). For example, the use of the compositions of the invention may improve the stability of the colour of the food or beverage fortified with iron (e.g. reduce the change in colour of the food or beverage as a result of iron fortification with the compositions of the invention in comparison with other iron compositions, such as ferrous sulphate).

A colour change may be considered to be a difference in colour of sufficient magnitude that a human observer would perceive the difference between two samples shown one after the other but not simultaneously. For example, a colour change may be considered to be a CIELAB ΔEab* colour difference greater than 2, for example greater than 3.0. In one embodiment, the compositions of the invention cause a CIELAB ΔEab* colour difference of less than 7, for example less than 6.5, 5.0, 4.5, 4.0, 3.5, 3.0, 2.5, 2.0 or 1.5, when used to fortify a food or beverage product, such as a product described herein. For example the compositions of the invention may be used to fortify a reconstituted bouillon at a Fe(III) level of between 15 and 25 mg per litre with a colour difference of less than 7 compared to an equivalent unfortified bouillon.

Organoleptic properties of foods and beverages may be readily measured by the skilled person. For example, the colour of food may be measured using the CIE 1976 L*a*b* (CIELAB) colour scale proposed by the Commission Internationale de l'Éclairage (CIE; CIE Technical Report, Colorimetry 2nd Edition, CIE 15.2 (1986, corrected reprint 1996)). The CIELAB colour space is produced by plotting the quantities L*, a*, b* in rectangular coordinates. The L* coordinate of an object is the lightness intensity as measured on a scale from 0 (black) to 100 (absolute white). The a* and b* coordinates have no specific numerical limits. The parameter a* runs from pure green (negative a*) to pure red (positive a*), while b* runs from pure blue (negative b*) to pure yellow (positive b*).

In the CIELAB colour space, colour difference may be calculated as a single value taking into account the differences between the L*, a* and b* values of two samples. The colour difference ΔEab* is calculated as follows:

$$\Delta Eab^* = \sqrt{(\Delta L^*)^2 + (\Delta a^*)^2 + (\Delta b^*)^2}$$

The compositions of the invention may reduce the effect of iron fortification on the organoleptic properties (e.g. colour or taste) of the food or beverage in comparison to other iron-fortifying compositions. For example, the use of the compositions of the invention may improve the stability of the colour of the food or beverage fortified with iron (e.g. reduce the change in colour of the food or beverage as a result of iron fortification with the compositions of the invention in comparison with other iron compositions, such as ferrous sulphate or ferric pyrophosphate).

The compositions of the invention may be used to prevent colour change over a food or beverage product's shelf-life. For example, the CIELAB ΔEab* colour difference between an iron-fortified food product at the time of its manufacture and the end of its shelf-life under recommended storage conditions may be less than 3.0, for example less than 2.0.

Shelf life is the recommended length of time that foods, beverages and many other perishable items can be stored during which the defined quality of a specified proportion of the goods remains acceptable under expected (or specified) conditions of distribution, storage and display. Typically a "best before date" (BBD) is printed on packaged perishable foods together with recommended storage conditions. Where such a BBD is indicated, the shelf-life is the time between manufacture and the BBD. Where a BBD is not indicated, the shelf-life is the equivalent period usual for the relevant product type.

The compositions of the invention may be used to prevent colour change during heat treatment of an iron-fortified food or beverage product. For example, the iron-fortified food or beverage product may have a ΔEab* value less than 3.0, for example less than 2.0, after a heat treatment of 2 minutes at 105° C.

In another embodiment, the use of the compositions of the invention increases the bioavailability of iron, in particular Fe(III), in a food or beverage, for example in comparison with other iron compositions, such as ferric pyrophosphate.

The dietary reference intake (DRI) for iron typically varies from 8 mg iron/person/day for adult men to 18 mg iron/person/day for menstruating women. The DRI is far greater for pregnant women, i.e. 27 mg iron/person/day. For breast-feeding mothers, the DRI is 9-10 mg iron/person/day.

The upper limit for iron is 45 mg iron/person/day for adults 19 years of age) and adolescents (14-18 years), and 40 mg iron/person/day for infants (0-12 months) and children (1-13 years).

The compositions of the invention may be useful in achieving the DRI for iron during the course of a subject's dietary intake.

The compositions of the invention may be any compositions that are suitable for ingestion by animals, preferably humans. The compositions may be ingested directly, however preferably the compositions of the invention are for use in fortifying foods and/or beverages with iron, i.e. increasing the amount of bioavailable iron in the food or beverage.

The food or beverage products to which the composition of the invention can be added include any product capable of being fortified with iron. Example food or beverage products include yoghurt, bouillon, water (e.g. bottled water), seasoning, sauce, milk powder, milk drink, milk-based dessert, pet food, cereal, pasta, noodle or baby food products.

In another aspect, the present invention provides a food or beverage product which has been fortified with the composition of the present invention, for example a food or beverage product obtainable by fortification with the composition of the present invention.

In one embodiment, the food or beverage product is a yoghurt, bouillon, water (e.g. bottled water), seasoning, sauce, milk powder, milk drink, milk-based dessert, pet food, cereal, pasta, noodle or baby food product. Preferably, the food or beverage product is a yoghurt, bouillon or water (e.g. bottled water).

Beverages are liquids consumed for refreshment or nourishment and include alcoholic and non-alcoholic drinks, carbonated drinks, fruit or vegetable juices and hot drinks, such as coffee or tea.

The compositions, or food or beverage products of the present invention may contain (e.g. may have been supplemented with) additional vitamins, minerals and micronutrients, including trace elements, in accordance with the recommendations (e.g. recommended daily intake guidelines) of government bodies.

The food or beverage products may comprise fruit or a component thereof. For example, the products may comprise fruit juice such as, but not limited to juice derived from an orange, apple, mango, peach, banana, date, apricot, grapefruit, papaya, pineapple, raspberry, strawberry, pear, tangerine and/or cherry.

The food or beverage products may, for example be fruit juice or may be in the form of a fruit puree which comprises fruit juice among other fruit components.

The food or beverage products may comprise fruit or a component thereof.

The problem of colour change when fortifying food with iron is particularly apparent with food compositions containing fruit. The colour of many fruits is derived from phenolic chromophore compounds and so addition of iron leads to a bathochromic shift in the colour of the phenolic chromophore compounds resulting in an undesirable change in the colour of the food.

Fruits are the fleshy seed-associated structure of a plant that are sweet and edible in the raw state, such as apples, oranges, grapes, strawberries and bananas. Fruits are often eaten as desserts in European cultures. The term fruit in the current specification includes seedless fruits such as seedless grapes and common varieties of bananas.

The fruit may, for example, be selected from the group consisting of blackcurrant, cranberry, elderberry, red currant, boysenberry, grape, cherry, orange, lemon, lime, mandarin, tangerine, grapefruit, pineapple, mango, papaya, passion fruit, kiwifruit, guava, fig, date, apple, plum, strawberry, raspberry, blueberry, blackberry, apricot, pear, banana, quince, wolfberry and mixtures of these.

The fruit may, for example, be in the form of fresh fruit, fresh fruit pieces, fruit powder, dried fruit or fruit puree.

Fruit intrinsically provides a good source of beneficial dietary nutrients, and so is a good basis for delivering additional nutritional benefits to food. There is therefore a need to provide iron-fortified food compositions containing fruit which do not exhibit undesirable colour changes.

The food or beverage products of the invention may be yoghurts or comprise yoghurts.

In the context of the present invention, the term "yoghurt" refers to a non-beverage food produced from the acidification of milk. Acidification is achieved through the addition of an acid, such as lemon juice or vinegar; through bacterial fermentation; or by a combination of acid addition and bacterial fermentation. The term "yoghurt" may include, but is not limited to, materials complying with local food labelling regulations concerning the term "yoghurt".

Yoghurt is a good source of calcium, helping to form and maintain strong bones. Yoghurt may also be fortified with other beneficial minerals such as magnesium and zinc. However, fortifying yoghurt with iron presents a problem if the yoghurt contains phenolic chromophore compounds, such as may be found in yoghurts containing fruit.

For example, a blueberry yoghurt, coloured by the anthocyanins in blueberries, will change colour after addition of iron; the anthocyanins undergoing a bathochromic shift. Similarly a banana yoghurt, which was initially a pale yellow colour, may develop an unattractive grey-blue colour on addition of iron. Bananas comprise polyphenols such as gallic acid, catechin, epicatechin and epigallocatechin.

The present invention provides iron-fortified food or beverage products comprising yoghurt where these colour change problems do not occur.

The food or beverage products of the invention may be bouillons.

Bouillons, also referred to as broths, are commonly used as flavourings during cooking. They may be prepared by heating (e.g. simmering) ingredients such as meat and/or bones (e.g. from beef or poultry), vegetables and/or herbs in water. Bouillons are regarded as particularly difficult to fortify with iron without affecting their organoleptic properties.

The bouillons may be in the form of dehydrated bouillons, for example bouillon cubes or granular bouillon. Such products are commonly used to add flavour during cooking.

The food or beverage products of the invention may be biscuit, cake or pastry products; a cereal bar; cereal, such as a breakfast cereal; an ice cream product; a dessert; a prepared meal; a nutritional supplement or a pet food product.

All of these products may pose problems of colour change when fortified by iron. For example biscuit, cake and pastry products may be coloured by natural colours such as anthocyanins or carmine; the products may have coloured fillings or coatings. Breakfast cereals may contain fruit, for example fruit inclusions or fruit fillings. Cereal bars may contain coloured fruit such as cranberries, or have coloured inclusions containing added vitamins and minerals, such as small chewy pieces of jelly. Ice creams and desserts may be coloured by anthocyanins, particularly when fruit flavoured. Prepared meals and nutritional supplements may contain fruits or vegetables for example in the form of vegetable powder, or may be coloured by the addition of natural colours to make them more appealing. Pet foods such as dog treats may contain fruit, for example berries. All these products may be sensitive to colour change on addition of iron, which may be reduced or eliminated by using the compositions of the invention.

The food or beverage products of the invention may be in the form of a therapeutic nutritional composition. The composition may be a nutritionally complete formula, for example including a source of protein, carbohydrate and fat.

In another aspect, the present invention provides a method of fortifying a food or beverage product comprising adding the composition of the invention to the food or beverage product.

In another aspect, the present invention provides a composition of the invention for use in the treatment or prevention of Iron Deficiency Anaemia (IDA). The composition may be for use in the prevention of IDA in individuals with medium to low iron status.

In another aspect, the present invention provides a method of preparing a water-soluble composition, wherein the method comprises the steps:

(a) mixing in an aqueous solution a source of Fe(III), phytic acid, hydrolysed protein and an acidity regulator; and (b) optionally heating the mixture, preferably to at least 50° C.

The acidity regulator may be an ammonium salt, for example the acidity regulator may be selected from the group consisting of ammonium hydroxide; ammonium carbonate; ammonium phosphate dibasic; ammonium sodium phosphate dibasic and triammonium phosphate. The acidity regulator may be ammonium hydroxide.

The hydrolysed protein may be hydrolysed plant protein, for example as described for the composition of the invention.

In one embodiment of the method of the invention, the mass ratio of phytic acid to Fe(III) is about 0.5:1 to about 125:1; the mass ratio of phytic acid to acidity regulator is about 0.1:1 to about 40:1; and/or the mass ratio of phytic acid to hydrolysed protein is about 0.5:1 to about 10:1.

The water-soluble composition prepared according to the method of the invention may be free from compounds comprising a carboxylic acid moiety other than those compounds comprised within the hydrolysed protein.

In one embodiment, the method further comprises the step of removing the water from the product obtained from step (a) or (b) to provide a solid composition. The water may be removed by any standard drying technique, such as freeze drying or spray drying. Preferably, the water is removed by freeze drying.

In one embodiment, the source of Fe(III) is selected from the group consisting of Fe(III) sulphate, Fe(III) citrate, Fe(III) diphosphate, Fe(III) saccharate, Fe(III) sodium diphosphate, Fe(III) choline citrate, Fe(III) ammonium citrate and Fe(III) chloride. Preferably, the source of Fe(III) is Fe(III) sulphate.

In one embodiment, step (b) of the method comprises heating the mixture to at least 60° C. In another embodiment, step (b) of the method comprises heating the mixture to at least 70° C. In another embodiment, step (b) of the method comprises heating the mixture to at least 80° C.

Following combination of all the components in step (a), it may be necessary to continue mixing until the composition dissolves. For example, it may be necessary to continue mixing for at least 6, 12, 18, 24, 30, 36, 42 or 48 hours. The time taken for the composition to dissolve may be reduced by heating the mixture, for example to at least 50° C., 60° C., 70° C. or 80° C.

By way of example, the method may comprise adding the source of Fe(III) (e.g. Fe(III) sulphate) to an aqueous phytic acid solution with stirring. The hydrolysed protein may then be added to the mixture in amounts necessary to provide the desired ratio of components. The acidity regulator may then be added to increase the pH of the mixture until the complex is solubilized.

The ratios of the individual components mixed in step (a) may be as described herein for the compositions of the invention.

Those skilled in the art will understand that they can freely combine all features of the present invention disclosed herein. In particular, features described for the compositions of the present invention may be combined with the method of the present invention and vice versa. Further, features described for different embodiments of the present invention may be combined. Where known equivalents exist to specific features, such equivalents are incorporated as if specifically referred to in this specification.

Further advantages and features of the present invention are apparent from the figure and non-limiting examples.

EXAMPLES

Example 1—Formation of the Complex

A double jacketed reactor was used to prepare the complex. The reactor was cooled down to 0° C. and phytic acid (Tongxiang Xinyang Food Additives Co., Ltd.) (solution 50%) in 40 mL water (MilliQ) was added under stirring (500 rpm). The temperature of the reactor was kept at 0° C. and ferric sulphate solution (Dr. P. Lohmann GmbH KG) in 40 mL water (MilliQ) was added drop-wise using a peristatic pump over at least 45 min. Once the solution was limpid (transparent), a protein hydrolysate in 30 mL water (Milli-Q®) was added and the mixture stirred for at least one hour. The temperature was then increased to 7° C. and the pH adjusted by a drop-wise addition of a solution of ammonium hydroxide ($NH_4OH$, 30%) until solubilisation of the complex (around pH 7.0, see table 1). The mixture was then pasteurized (65° C., 30-40 min) and freeze-dried.

Twelve samples were prepared with different levels of phytic acid, Fe(III), ammonium hydroxide and protein hydrolysate. The weight of each component (dry basis) in the different samples is given in table 1.

Samples 1 to 5 used an acid hydrolysed soy protein hydrolysate (degree of hydrolysis 80 w/w %) (Sigma), sample 6 used an acid hydrolysed soy protein hydrolysate (degree of hydrolysis 75 w/w %) (Exter), sample 7 used an acid hydrolysed wheat protein hydrolysate (degree of hydrolysis 75 w/w %) (Exter), samples 8 and 9 used an acid hydrolysed corn protein hydrolysate (degree of hydrolysis 75 w/w %) (Exter), sample 10 used an enzymatically hydrolysed soy bean protein hydrolysate (degree of hydrolysis 20 w/w %) (VP-2000, Three-A (Qinhuangdao) Food Industries Co., Ltd., China) whereas sample 11 used a non-hydrolysed soy protein (Soy protein isolate Clarisoy 100 from ADM, Switzerland). The degree of hydrolysis was between 70 and 100 w/w % for the acid hydrolysed samples and between 20 and 30 w/w % for the enzymatically hydrolysed sample.

All the samples formed a soluble complex except for sample 11, where a non-hydrolysed protein was used. The Fe(III) content and phosphorous content of each freeze-dried complex was measured analytically and is shown in table 1.

Example 2—Colour Change in Iron-Fortified Bouillon

Commercial Maggi Chicken Bouillon (Nestle Nigeria) containing curcumin was iron fortified by the addition of iron (III) complexes from Example 1, as well as ferrous sulphate (Dr. P. Lohmann GmbH KG) Ref1, and ferric pyrophosphate (Dr. P. Lohmann GmbH KG) Ref2. The amounts were chosen to provide approximately 5.5 mg of iron per 6.55 g of bouillon powder. A further sample without iron fortification was also prepared in the same manner. All samples were reconstituted in 250 mL of boiling water and kept at 60° C. for a minimum of 30 minutes.

Colour measurements were performed in 2.6×1 cm quartz cuvettes using an XRite ColorEye 7000A colorimeter. The colorimeter was set up with a D65 light source, 10 degree observer angle, specular component included and Large area View (LAV). The colour difference between the beverage with no iron salt and the iron-fortified beverages was measured for each material and expressed as ΔEab* using the CIELAB colour scale (Table 2).

TABLE 2

| | iron fortified bouillon colour stability | |
|---|---|---|
| Sample No. | Protein source | Δ E |
| 1 | Soy | 7.2 |
| 2 | Soy | 6.4 |
| 3 | Soy | 6.6 |
| 4 | Soy | 7.3 |
| 5 | Soy | 6.9 |
| 6 | Soy | 7.3 |
| 7 | Wheat | 7.1 |
| 9 | Corn | 6.7 |
| 10 | Soy | 6.4 |
| Ref1 | Ferrous Sulphate | 15.2 |
| Ref2 | Ferric Pyrophosphate | 6.1 |

The bouillon fortified with iron (III) complexes from Example 1 showed a much lower colour change than the bouillon fortified by ferrous sulphate.

TABLE 1

| | | | | | | | | |
|---|---|---|---|---|---|---|---|---|
| | | | complexes | | | | | |
| Sample No. | Protein source | Pure Phytic acid (g) | Fe(III) (g) | Protein hydrolysates (g) | Ammonium hydroxide (g) | pH | Fe(III) content (%) | Phosphorus content (%) |
| 1 | Soy | 10 | 1.4 | 3.5 | 25 | 7.0 | 4.5 | 7.3 |
| 2 | Soy | 10 | 1.4 | 7.0 | 21 | 6.8 | 4.7 | 6.5 |
| 3 | Soy | 10 | 1.1 | 3.5 | 24 | 6.7 | 4.3 | 12.5 |
| 4 | Soy | 11 | 1.4 | 3.6 | 27 | 6.8 | 5.1 | 12.4 |
| 5 | Soy | 50 | 7.2 | 20.4 | 73.8 | 5.8 | 5.1 | 12.4 |
| 6 | Soy | 11 | 1.4 | 3.6 | 25 | 7.0 | 4.3 | 12.3 |
| 7 | Wheat | 10 | 1.4 | 3.6 | 25 | 7.2 | 4.4 | 12.4 |
| 8 | Corn | 11 | 1.4 | 3.6 | 25 | 7.2 | 4.4 | 12.7 |
| 9 | Corn | 6.2 | 0.76 | 2.2 | 10.5 | 6.8 | 4.7 | 13.9 |
| 10 | Soy | 6.2 | 0.72 | 2.1 | 11.5 | 6.2 | 4.3 | 13.6 |
| 11 | Soy | 10 | 1.4 | 3.5 | 25 | 6.8 | — | — |

Example 3—In-Vitro Bioaccessiblity Tests

For iron fortificants, in-vitro dissolution in gastric conditions is considered a good indicator of the relative biological value (i.e., bioavailability) [Comparison of in-vitro, animal, and clinical determinations of iron bioavailability: International Nutritional Anemia Consultative Group Task Force report on iron bioavailability, Am J Clin Nutr 1989;49:225-38]. The experiment consists of measuring the free iron concentration in 0.02M HCL (with nominal pH of 1.7 units) under orbital agitation at 37° C. for 90 minutes. After 90 minutes the pH is adjusted to neutral with 1M NaOH and the concentration determined for another 30 minutes at the above temperature. The initial period at pH 1.7 is to simulate stomach digestion and the period at pH 7 simulates the intestine tract.

A selection of the complexes from Example 1 (samples 4, 6, 7, 8, 9 and 10) were compared to ferrous sulphate and ferric pyrophosphate. The target of 60 mg/L was fixed for all samples. Fe content in solution was measured by Atomic Emission Spectroscopy and the values were converted in percentage relative bioaccessibility as shown in FIG. 1.

From FIG. 1 it can be seen that ferrous sulphate ($FeSO_4$) is readily soluble at acidic pH but precipitation occurs at neutral pH. Ferric pyrophosphate (FePP) is not soluble at either of the two pH levels. The complexes of Fe(III), phytic acid, hydrolysed protein and an acidity regulator are readily soluble and are not altered by the pH variation. As solubility is a significant factor in bioavailability, this indicates a potential better bioavailability for the complexes than for $FeSO_4$ or FePP.

Example 4—Bioaccessiblity Using Caco-2 Cell Models

Samples of chicken bouillon were prepared with a 2.1 mg of iron for 3.3 g of commercial chicken bouillon mass through dry mixing. Once fortified each bouillon sample was split in 5 fractions. Three fractions were analysed to check Fe homogeneity in the sample and the other two fractions were submitted to the Caco-2 cell test.

The iron sources were; Phytic acid:Fe (Ref3), Phytic acid:Fe:hydrolysed soy proteins (Sample 4), $FeSO_4$(Ref1) and Ferric Pyrophosphate (Ref2).

The phytic acid:Fe complex was prepared by dissolving sodium phytate (123.4 g) in demineralized water (1.4 L) under stirring. The pH was adjusted to 1.7 with 3M HCl. Ferric Sulphate (46.4 g was dissolved in 0.6 L demineralized water until completely dissolved. The pH was adjusted to 1.7 with 3M HCl. The ferric sulphate solution was added into the sodium phytate solution using a peristaltic pump at 300 ml per hour. The mixture was stirred for 14 hours at room temperature. The sample was filtered and freeze-dried. The complex contained 9% iron by weight.

Bioaccessiblity of PA:Fe:AA complexes were measured during digestion and uptake via Caco-2 cells. In short, the bouillon samples fortified by the different iron compounds were reconstituted (13.1 g bouillon mass in 500 mL boiling water). The samples were then in-vitro digested and fed to the cell culture. Analysis was performed at Cornell University according to the method of Glahn et al. [Glahn et al., Journal of Nutrition, 128(9), 1555-1561. (1998)] Relative iron bioaccessibility (% RBA) values were calculated by dividing the ferritin value for each sample by the ferritin value of ferrous sulphate heptahydrate.

Figure 2:
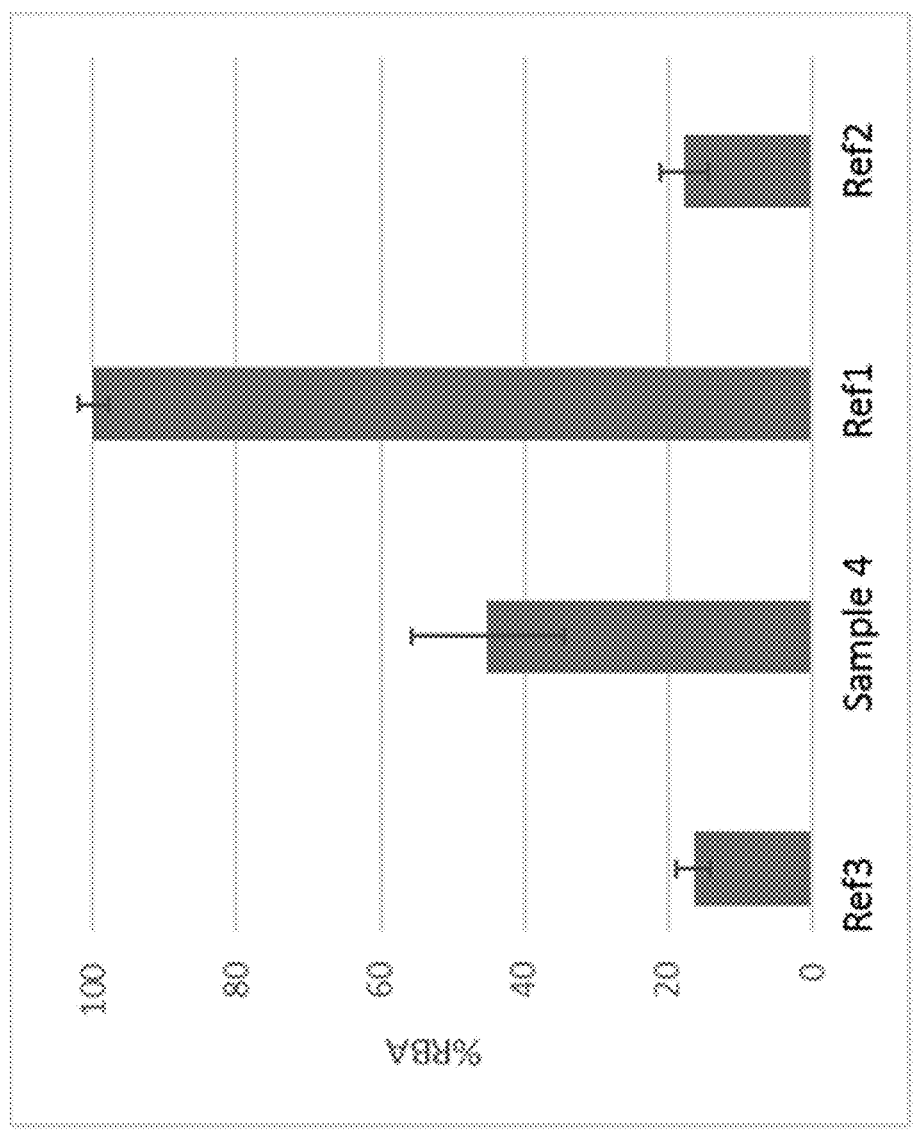
FIG. 2 shows Caco-2 bioaccessibility data comparing different iron compounds; phytic acid:Fe (Ref3), phytic acid:Fe:hydrolysed soy protein (Sample4), FeSO$_4$ (Ref1) and Fe pyrophosphate (Ref2).

Results are plotted in FIG. 2. The bioaccessibility of the Fe(III):phytic acid:hydrolysed protein complex was greater than both the iron phytic acid complex and ferric pyrophosphate (p<0.05) and approximately 50% of the RBA value obtained with ferrous sulphate (the recognized iron compound for food fortification in humans in terms of high absorption but which causes sensory changes in the food vehicle in the presence of polyphenols or high amounts of unsaturated lipids).

Example 5—Bioavailability Study of Phytic Acid:Iron:Hydrolysed Corn Protein Complex (PA:Fe:HCP)

Clinical trials were performed on fortified chicken bouillon and fortified chicken bouillon with corn flour to simulate inhibitory conditions. The trial was performed by ETH Zurich (Switzerland). The study was a controlled, single blind, single centre, and randomized cross-over trial in 22 healthy adult women, with each woman serving as her own control. Each participant consumed 6 different types of investigational products: bouillon respectively bouillon with maize porridge fortified either with PA:$^{58}$Fe:HCP, $^{54}$FeSO$_4$, (Ref1-labelled) or $^{57}$FePP (Ref2-labelled). The PA:$^{58}$Fe:HCP complex was prepared as Example 1 sample 9 apart from the use of $^{58}$Fe. The order of test meal administration was randomly assigned. The experimental phase lasted for a period of 33 days.

Test Meal Preparation and Iron Fortification

The bouillon meal was prepared from 300 g ultrapure water and 7 g commercial vegetable bouillon powder per serving. The inhibitory meal was a corn porridge, prepared from 300 g ultrapure water, 7 g commercial vegetable bouillon powder and 50 g whole corn flour per serving (Farina per polenta integrale, Paolo Bassetti—PA:Fe=5:1 mol ratio). Test meals were prepared fresh the day before each feeding and stored in individual portions in a refrigerator overnight. On the day of administration, test meals were heated in a microwave oven. The pre-weighed vials containing the labelled Fe compounds were added to the test meals and were rinsed 2 times with 2 mL of ultrapure water. Subjects received a total of 4.2 mg iron per test meal, equivalent to 19 mg of [$^{57}$Fe]-PP, 12 mg of [$^{54}$Fe]-SO$_4$ and 80 mg of [$^{58}$Fe]-PA-HCP. Test meals were stirred and served to the participants for complete consumption.

Subjects

Inclusion criteria were as follows: 1) women aged 18-40 yrs; 2) healthy, based on the medical screening visit; 3) BMI of 18.5-25.0 kg/m$^2$; 4) weight less than 65 kg. Exclusion criteria were as follows: 1) anemia or polycythemia (evidenced one of the following parameters being out of range: number of erythrocytes 4.0-5.8 T/L, hemoglobin (Hb) 120-160 g/l, hematocrit (Ht) 35-55%); 2) significant blood loss over the past 6 months; 3) plasma ferritin >80 pg/L, chosen to exclude subjects with hemochromatosis; 4) any therapy or medication taken for infectious and/or inflammatory disease in the past two weeks; 5) relevant digestive, renal and/or metabolic disease; 6) diagnosed food allergy; 7) pregnancy (tested in plasma at screening) and/or lactation; 8) history of cancer within the past year; 9) 10% or more weight loss during the last 3 months; 10) any medication or supplement which may impact erythrocytes, Hb or Ht; 11) iron supplementation therapy or perfusion in the last three months; 12) smoking; 13) high alcohol consumption (>2 drinks/day); 14) consumption of illicit drugs.

Study Procedures

The labelled iron-fortified test meals were administered on days 1, 2, 3, 17, 18 and 19. Test meals were administered between 07.00 and 09.30 after an overnight fast. The participants consumed the complete test meal and a glass of 300 ml ultrapure water in the presence of the investigators.

Quantitative consumption of the investigational product was ensured by washing the glass test meal container 2 times with 10 mL of ultrapure water. After consuming the test meals, participants were not allowed to eat or drink for 3 h.

Calculation of Iron Bioavailability

Fractional iron absorption (FIA) was calculated based on the measured shift of iron isotope ratios in the blood 14 days after the test meal administrations, from the blood samples collected on days 1, 17 and 35. For the calculation on day 35, the isotopic ratio of day 17 was considered as a new baseline. The amounts of $^{54}$Fe, $^{57}$Fe and $^{58}$Fe in the blood were calculated on the principle of isotope dilution by considering that iron isotopic labels are not mono-isotopic. Circulating iron was calculated based on blood volume and hemoglobin concentration. Blood volume was indirectly measured based on height and weight and calculated using the formula proposed by Brown et al [E. Brown et al., The Journal of clinical investigation, 41:21, 82-90.(1962)]. For calculations of fractional absorption, 80% incorporation of the absorbed iron into red blood cells was assumed.

Figure 3:
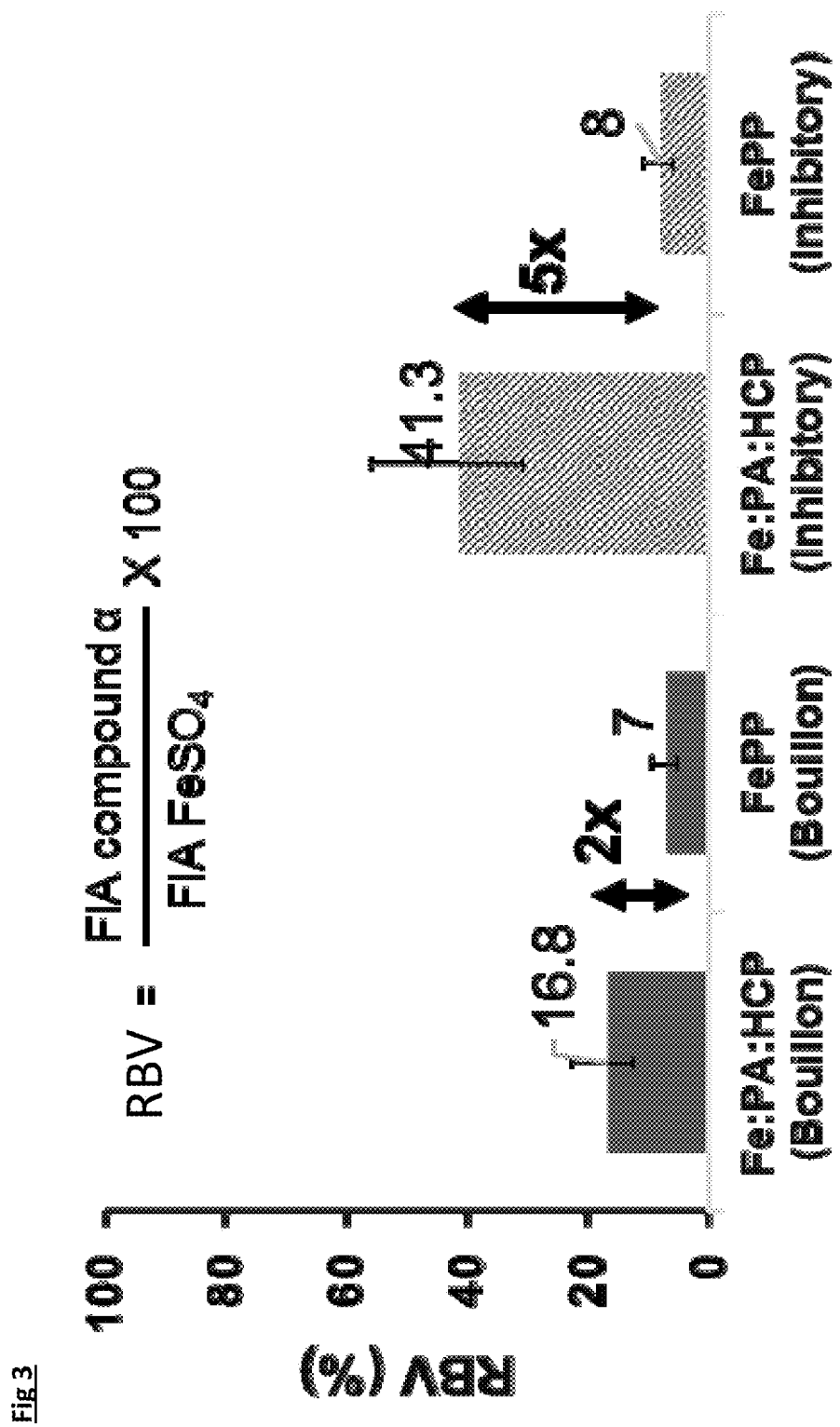
FIG. 3 is a plot of relative iron bioavailability (RBV) of labelled PA:58Fe:HCP (Sample 9—58Fe labelled) to 54FeSO4 and of 57FePP to 54FeSO4 from fortified reconstituted bouillons and from fortified reconstituted bouillons co-ingested with a high inhibitory meal rich in phytate.

The nutritional value of the Fe:PA:HCP complexes was assessed in a randomized controlled, single blind, cross-over human study conducted at the laboratory of human nutrition of university of Zurich (ETHZ). In this study, the absorption of iron in healthy adult women (n=22) from bouillon fortified with isotopically labelled PA:$^{58}$Fe:HCP, $^{57}$FePP and $^{54}$FeSO$_4$ was assessed with and without the addition of an inhibitory maize meal rich in phytate. Iron absorption was assessed by means of erythrocyte incorporation 14 d after consumption of the labelled test meals. Results are presented in FIG. 3.

The RBV of PA:$^{58}$Fe:HCP was 2× and 5× higher than the RBV of $^{57}$FePP consumed in bouillon and bouillon with maize meal rich in phytate respectively. This larger difference in RBV of PA:$^{58}$Fe:HCP observed in the inhibitory meal versus bouillon alone can be explained as result of the large variability of fractional iron absorption of $^{54}$FeSO$_4$ in bouillon (24.6%) when compared to $^{54}$FeSO$_4$ in bouillon plus maize meal rich in phytate (3.6%).

A complex of Fe(III), phytic acid, hydrolysed protein and an acidity regulator was found to provide a more nutritious alternative to FePP for fortification of food such as bouillon cubes. It is especially effective when co-ingested with an inhibitory meal and in individuals with medium to low iron status.

The invention claimed is:

1. A method of treatment or prevention of Iron Deficiency Anaemia (IDA) in an individual in need thereof, the method comprising administering a composition comprising a complex to the individual, the complex comprising Fe(III), phytic acid, hydrolysed protein and an acidity regulator.

2. The method of claim 1 wherein the complex has at least one formulation selected from the group consisting of:
   (a) the mass ratio of phytic acid to Fe(III) is about 0.33:1 to about 125:1;
   (b) the mass ratio of phytic acid to the acidity regulator is about 0.1:1 to about 40:1; and
   (c) the mass ratio of phytic acid to the hydrolysed protein is about 0.5:1 to about 10:1.

3. The method of claim 1, wherein the acidity regulator is selected from the group consisting of ammonium hydroxide, ammonium carbonate, ammonium phosphate dibasic, ammonium sodium phosphate dibasic, triammonium phosphate, and mixtures thereof.

4. The method of claim 1, wherein the hydrolysed protein in the complex is protein hydrolysed to at least 10 w/w %.

5. The method of claim 1, wherein the composition is an aqueous solution or a water-soluble solid.

6. The method of claim 1, wherein the hydrolysed protein in the complex comprises a hydrolysed plant protein.

7. The method of claim 1, wherein the complex is made by a process comprising mixing an iron source with the phytic acid, the hydrolysed protein and the acidity regulator, wherein the iron source comprises the Fe(III) and is selected from the group consisting of Fe(III) sulphate, Fe(III) citrate, Fe(III) diphosphate, Fe(III) saccharate, Fe(III) sodium diphosphate, Fe(III) choline citrate, Fe(III) ammonium citrate, and Fe(III) chloride.

8. The method of claim 1, wherein the composition is free from compounds comprising a carboxylic acid moiety other than those compounds comprised within the hydrolysed protein.

9. The method of claim 1, wherein the hydrolysed protein in the complex is protein hydrolysed between 70 and 100 w/w %.

10. The method of claim 1, wherein the hydrolysed protein in the complex comprises at least 10 mg/g of histidine, at least 50 mg/g of arginine, at least 50 mg/g of lysine, at least 30 mg/g of glycine, at least 90 mg/g of aspartic acid, at least 100 mg/g of glutamine, and at least 30 mg/g of proline.

11. The method of claim 1, wherein the hydrolysed protein in the complex comprises a mixture of free amino acids, free peptides, and non-hydrolysed proteins.

12. The method of claim 11, wherein the amount of free amino acids is selected from the group consisting of
   (a) between 15 and 45 wt. %, and
   (c) between 65 and 85 wt. %.

13. The method of claim 1, wherein the complex has at least one formulation selected from the group consisting of:
   (a) the mass ratio of the phytic acid to the Fe(III) is between 5:1 and 10:1;
   (b) the mass ratio of the phytic acid to the hydrolysed protein is between 1:1 and 3.5:1;
   (c) the acidity regulator is ammonium hydroxide added in an amount to adjust the pH to between 6.5 and 7.5; and
   (d) the hydrolysed protein is hydrolysed to an extent greater than 20 w/w %.

14. The method of claim 1, wherein the mass ratio of the phytic acid to the Fe(III) in the complex is about 0.5:1 to about 125:1.

15. The method of claim 1, wherein the mass ratio of the phytic acid to the acidity regulator in the complex is about 0.1:1 to about 40:1.

16. The method of claim 1, wherein the mass ratio of the phytic acid to the hydrolysed protein in the complex is about 0.5:1 to about 10:1.

17. The method of claim 1, wherein the molar ratio of the phytic acid to the Fe(III) in the complex is about 0.25:1 to about 10:1.

18. The method of claim 1, wherein the molar ratio of the phytic acid to the acidity regulator in the complex is about 0.005:1 to about 2:1.

19. The method of claim 1, wherein the molar ratio of the acidity regulator to the Fe(III) in the complex is about 4:1 to about 30:1.

* * * * *